United States Patent [19]
Rhee et al.

[11] Patent Number: 5,470,911
[45] Date of Patent: Nov. 28, 1995

[54] GLYCOSAMINOGLYCAN-SYNTHETIC POLYMER CONJUGATES

[75] Inventors: Woonza M. Rhee, Palo Alto; Richard A. Berg, Los Altos, both of Calif.

[73] Assignee: Collagen Corporation, Palo Alto, Calif.

[21] Appl. No.: 433,656

[22] Filed: May 4, 1995

Related U.S. Application Data

[60] Division of Ser. No. 146,843, Nov. 3, 1993, which is a continuation-in-part of Ser. No. 907,518, Jul. 2, 1992, Pat. No. 5,324,775, which is a continuation-in-part of Ser. No. 433,441, Nov. 14, 1989, Pat. No. 5,162,430, which is a continuation-in-part of Ser. No. 274,071, Nov. 21, 1988, abandoned.

[51] Int. Cl.$^6$ .......................... C08G 63/48; C08G 63/91; C08G 63/40
[52] U.S. Cl. .......................... 525/54.1; 525/54.2; 525/937; 530/402
[58] Field of Search .................................. 525/54.1, 54.2, 525/937; 530/402, 356; 523/113

Primary Examiner—Nathan M. Nutter
Attorney, Agent, or Firm—Kathi Rafayko

[57] ABSTRACT

Pharmaceutically acceptable, nonimmunogenic compositions are formed by covalently binding glycosaminoglycans or derivatives thereof, to hydrophilic synthetic polymers via specific types of chemical bonds to provide biocompatible conjugates. Useful glycosaminoglycans include hyaluronic acid, the chondroitin sulfates, keratan sulfate, chitin and heparin, each of which is chemically derivatized to react with a hydrophilic synthetic polymer. The conjugate comprising a glycosaminoglycan covalently bound to a hydrophilic synthetic polymer may be further bound to collagen to form a three component conjugate having different properties. The hydrophilic synthetic polymer may be polyethylene glycol and derivatives thereof having an average molecular weight over a range of from about 100 to about 100,000. The compositions may include other components such as fluid, pharmaceutically acceptable carriers to form injectable formulations, and/or biologically active proteins such as growth factors or cytokines. The conjugates of the invention generally contain large amounts of water when formed. The conjugates can be dehydrated to form a relatively solid implant for use in hard tissue augmentation. The dehydrated, solid implant can further be ground into particles which can be suspended in a non-aqueous fluid and injected into a living being (preferably human) for soft tissue augmentation. Once in place, the solid implants or particles rehydrate and expand in size approximately three- to five-fold.

8 Claims, No Drawings

GLYCOSAMINOGLYCAN-SYNTHETIC POLYMER CONJUGATES

CROSS-REFERENCES

This application is a Divisional of copending U.S. application Ser. No. 08/146,843, filed Nov. 3, 1993, which is a continuation-in-part of U.S. application Ser. No. 07/907,518, filed Jul. 2, 1992, and now U.S. Pat. No. 5,324,775, issued Jun. 28, 1994, which is a continuation-in-part of U.S. application Ser. No. 07/433,441, filed Nov. 14, 1989, and now U.S. Pat. No. 5,162,430, issued Nov. 10, 1992, which is a continuation-in-part of U.S. application Ser. No. 07/274,071, filed Nov. 21, 1988, subsequently abandoned, which applications and issued patents are incorporated herein by reference in full and to which we claim priority under 35 USC §120.

FIELD OF THE INVENTION

This invention relates to biocompatible conjugates and, specifically, to pharmaceutically acceptable, nonimmunogenic compositions comprising one or more glycosaminoglycans, or derivatives thereof, conjugated to a synthetic hydrophilic polymer such as polyethylene glycol (PEG), which is optionally conjugated to collagen as well.

BACKGROUND OF THE INVENTION

Daniels et al, U.S. Pat. No. 3,949,073, disclosed the preparation of soluble collagen by dissolving tissue in aqueous acid, followed by enzymatic digestion. The resulting atelopeptide collagen is soluble, and substantially less immunogenic than unmodified collagen. It may be injected into suitable locations of a subject with a fibril-formation promoter (described as a polymerization promoter in the patent) to form fibrous collagen implants in situ, for augmenting hard or soft tissue. This material is now commercially available from Collagen Corporation (Palo Alto, Calif.) under the trademark Zyderm® Collagen Implant.

Luck et al, U.S. Pat. No. 4,488,911, disclosed a method for preparing collagen in solution (CIS), wherein native collagen is extracted from animal tissue in dilute aqueous acid, followed by digestion with an enzyme such as pepsin, trypsin, or Pronase®, a trademark of American Hoechst Corporation, Somerville, N.J. The enzymatic digestion removes the telopeptide portions of the collagen molecules, providing "atelopeptide" collagen in solution. The atelopeptide CIS so produced is substantially nonimmunogenic, and is also substantially non-crosslinked due to loss of the primary crosslinking regions. The CIS may then be precipitated by dialysis in a moderate shear environment to produce collagen fibers which resemble native collagen fibers. The precipitated, reconstituted fibers may additionally be crosslinked using a chemical agent (for example, aldehydes such as formaldehyde and glutaraldehyde), heat, or radiation. The resulting products are suitable for use in medical implants due to their biocompatability and reduced immunogenicity.

Wallace et al, U.S. Pat. No. 4,424,208, disclosed an improved collagen formulation suitable for use in soft tissue augmentation. Wallace's formulation comprises reconstituted fibrillar atelopeptide collagen (for example, Zyderm® Collagen) in combination with particulate, crosslinked atelopeptide collagen dispersed in an aqueous medium. The addition of particulate crosslinked collagen improves the implant's persistence, or ability to resist shrinkage following implantation.

Smestad et al, U.S. Pat No. 4,582,640, disclosed a glutaraldehyde crosslinked atelopeptide CIS preparation (GAX) suitable for use in medical implants. The collagen is crosslinked under conditions favoring intrafiber bonding rather than interfiber bonding, and provides a product with higher persistence than non-crosslinked atelopeptide collagen. Said product is commercially available from Collagen Corporation under the trademark Zyplast® Collagen Implant.

Nguyen et al, U.S. Pat. No. 4,642,117, disclosed a method for reducing the viscosity of atelopeptide CIS by mechanical shearing. Reconstituted collagen fibers are passed through a fine-mesh screen until viscosity is reduced to a practical level for injection.

Nathan et al, U.S. Pat. No. 4,563,350, disclosed osteoinductive bone repair compositions comprising an osteoinductive factor, at least 5% nonreconstituted (afibrillar) collagen, and the remainder reconstituted collagen and/or mineral powder (e.g., hydroxyapatite). CIS may be used for the nonreconstituted collagen, and Zyderm® Collagen Implant (ZCI) is preferred for the reconstituted collagen component. The material is implanted in bone defects or fractures to speed ingrowth of osteoclasts and promote new bone growth.

Chu, U.S. Pat. No. 4,557,764, disclosed a "second nucleation" collagen precipitate which exhibits a desirable malleability and putty-like consistency. Collagen is provided in solution (e.g., at 2–4 mg/mL), and a "first nucleation product" is precipitated by rapid titration and centrifugation. The remaining supernatant (containing the bulk of the original collagen) is then decanted and allowed to stand overnight. The precipitated second nucleation product is collected by centrifugation.

Chu, U.S. Pat. No. 4,689,399, disclosed a collagen membrane preparation, which is prepared by compressing and drying a collagen gel. The resulting product has high tensile strength.

Silver et al., U.S. Pat. No. 4,703,108, disclosed the preparation of a sponge prepared by crosslinking insoluble collagen using dehydrothermal means or by using cyanamide. Berg et al., U.S. Pat. No. 4,837,285, disclosed the preparation of collagen in bead form for soft tissue augmentation. Brodsky et al., U.S. Pat. No. 4,971,954, have disclosed a method of crosslinking collagen using ribose or other reducing sugars.

Miyata et al., Japanese patent application 4-227265, published Aug. 17, 1992, discloses a composition comprised of atelopeptide collagen linked to a polyepoxy compound. The composition is injected into the body to obtain sustained skin-lifting effects.

J. A. M. Ramshaw et al, *Anal Biochem* (1984) 141:361–65, and PCT application WO87/04078, disclosed the precipitation of bovine collagen (types I, II, and III) from aqueous PEG solutions, where there is no binding between collagen and PEG.

Werner, U.S. Pat. No. 4,357,274, disclosed a method for improving the durability of sclero protein (e.g., brain meninges) by soaking the degreased tissue in hydrogen peroxide or polyethylene glycol for several hours prior to lyophilization. The resulting modified whole tissue exhibits increased persistence.

Hiroyoshi, U.S. Pat. No. 4,678,468, disclosed the preparation of polysiloxane polymers having an interpenetrating network of water-soluble polymer dispersed within. The water-soluble polymer may be a collagen derivative, and the polymer may additionally include heparin. The polymers are shaped into artificial blood vessel grafts, which are designed to prevent clotting.

Other patents disclose the use of collagen preparations incorporating bone fragments or minerals. For example, Miyata et al, U.S. Pat. No. 4,314,380, disclosed a bone implant prepared by baking animal bone segments, then soaking the baked segments in a solution of atelopeptide collagen. Deibig et al, U.S. Pat. No. 4,192,021, disclosed an implant material which comprises powdered calcium phosphate in a pasty formulation with a biodegradable polymer (which may be collagen). Commonly owned U.S. application Ser. No. 06/855,004, filed Apr. 22, 1986, now abandoned, disclosed a particularly effective bone repair material comprising autologous bone marrow, collagen, and particulate calcium phosphate in a solid, malleable formulation.

There are several references in the art to proteins modified by covalent conjugation to polymers to alter the solubility, antigenicity, and biological clearance of the protein. For example, U.S. Pat. No. 4,261,973 disclosed the conjugation of several allergens to PEG or PPG (polypropylene glycol) to reduce the proteins' immunogenicity. U.S. Pat. No. 4,301,144 disclosed the conjugation of hemoglobin with PEG and other polymers to increase the protein's oxygen-carrying capability. EPO 98,110 disclosed coupling an enzyme or interferon to a polyoxyethylene-polyoxypropylene (POE-POP) block polymer to increase the protein's half-life in serum. U.S. Pat. No. 4,179,337 disclosed conjugating hydrophilic enzymes and insulin to PEG or PPG to reduce immunogenicity. Davis et al, *Lancet* (1981) 2:281–83, disclosed the enzyme uricase modified by conjugation with PEG to provide uric add metabolism in serum having a long half-life and low immunogenicity. Nishida et al, *J Pharm Pharmacol* (1984) 36:354–55, disclosed PEG-uricase conjugates administered orally to chickens, demonstrating decreased serum levels of uric acid. Inada et al, *Biochem & Biophys Res Comm* (1984) 122:845–50 disclosed lipoprotein lipase conjugated with PEG to render it soluble in organic solvents. Takahashi et al, *Biochem & Biophys Res Comm* (1984) 121:261–65, disclosed HRP conjugated with PEG to render the enzyme soluble in benzene. Abuchowski et al, *Cancer Biochem Biophys* (1984) 7:175–86, disclosed that enzymes such as asparaginase, catalase, uricase, arginase, trypsin, superoxide dismutase, adenosine deaminase, phenylalanine ammonia-lyase and the like conjugated with PEG exhibit longer half-lives in serum and decreased immunogenicity. However, these references are essentially concerned with modifying the solubility and biological characteristics of proteins administered in low concentrations in aqueous solution.

M. Chvapil et al, *J Biomed Mater Res* (1969) 3:315–32, disclosed a composition prepared from collagen sponge and a crosslinked ethylene glycol monomethacrylate-ethylene glycol dimethacrylate hydrogel. The collagen sponge was prepared by lyophilizing an aqueous mixture of bovine hide collagen and methylglyoxal, a tanning agent. The sponge-hydrogel composition was prepared by polymerizing ethylene glycol monomethacrylate and ethylene glycol dimethacrylate in the sponge.

A series of related patents disclose various types of collagen-containing materials. The patents are U.S. Pat. No. 4,703,108, issued Oct. 27, 1987; U.S. Pat. No. 4,861,714, issued Aug. 29, 1989; U.S. Pat. No. 4,863,856, issued Sep. 5, 1989; U.S. Pat. No. 4,925,924, issued May 15, 1990; 4,970,298, issued Nov. 13, 1990; and U.S. Pat. No. 4,997,753, issued Mar. 5, 1991. All of these patents disclose collagen materials wherein type I, II, and III collagens are contacted with a crosslinking agent selected from the group consisting of a carbodimide or a succinimidyl active ester. Various types of treatment may be carried out prior to or after crosslinking in order to form particular types of desired materials such as sponges and/or sheets.

In U.S. Pat. No. 5,162,430, we described chemical conjugates whereby various forms of collagen were conjugated using synthetic hydrophilic polymers such as polyethylene glycol. Such conjugates are useful for a variety of applications, such as soft tissue augmentation and the formation of implants useful in bone repair. In U.S. application Ser. No. 07/907,518, we disclose that it is possible to form such conjugates with biomaterials other than collagen. Specifically, synthetic hydrophilic polymers are used to crosslink insoluble biocompatible, biologically inert (preferably naturally occurring) polymers other than collagen. Activated polyethylene glycol is the preferred crosslinking agent. We now describe specific biocompatible polymer conjugates and their methods of synthesis, which include conjugates of glycosaminoglycans, and/or their derivatives, which can be used in a manner similar to the collagen-polymer conjugates described in our earlier, above-referenced U.S. Pat. No. 5,162,430, which is incorporated herein by reference.

SUMMARY OF THE INVENTION

Biocompatible, pharmaceutically acceptable, nonimmunogenic conjugates are formed by covalently binding glycosaminoglycans, and/or derivatives thereof, to a synthetic hydrophilic polymer, such as an activated polyethylene glycol, and optionally covalently binding the conjugate to collagen.

The synthetic hydrophilic polymer is preferably an activated polyethylene glycol or a derivative thereof having an average molecular weight in the range of about 100 to about 100,000, preferably between 1,500 to 20,000. Compositions comprising the conjugates may optionally include other components such as pharmaceutically acceptable fluid carriers to form injectable formulations, and/or biologically active proteins such as cytokines or growth factors. The biocompatible conjugates of the invention generally contain large amounts of water when formed. The conjugates can be dehydrated to form relatively solid implants for hard tissue augmentation, such as the repair or replacement of bone or cartilage. The dehydrated, solid implant can further be gound into particles which can be suspended in a nonaqueous fluid and injected into a living being for soft tissue augmentation. Once in place, the solid implants or particles rehydrate and expand in size five-fold or more.

The invention relates to biocompatible conjugates which may be used in a variety of medical and pharmaceutical applications. The most basic embodiment includes the biocompatible conjugates and pharmaceutical compositions formulated using these conjugates, which may additionally include pharmaceutically acceptable carriers in different types and amounts. The conjugates include a synthetic hydrophilic polymer, one or more type of glycosaminoglycan, and optionally, collagen.

One of the most important uses for the conjugates and compositions of the invention is in soft tissue augmentation. The compositions are formulated into a flowable form and injected into patients, such as into facial areas, for the purpose of soft tissue augmentation. The method can be varied so that the reaction between the glycosaminoglycan and the synthetic polymer occurs in situ. Furthermore, the conjugates can be dehydrated and then ground into particles, suspended in an inert nonaqueous carrier, and injected into a patient. After injection, the carrier will be removed by natural physiological conditions and the particles will rehydrate and swell to their original size.

The conjugates can further be molded into a desired shape, then dehydrated to form a solid implant for use in hard tissue augmentation, such as for the repair or replacement of cartilage or bone.

The conjugates of the invention can be combined with cytokines or growth factors. The cytokines can be either simply admixed with the glycosaminoglycan-synthetic polymer conjugate, or can be chemically conjugated to di- or multi-functionally activated polymer (e.g., glycosaminoglycan-synthetic polymer-cytokine). In the case of an admixture, the cytokines or growth factors are not chemically bound to the conjugate and may diffuse out from the site of administration into the surrounding tissue, providing for sustained release and local therapeutic effects. In the case of the cytokine or growth factor being chemically conjugated to the polymer conjugate, the cytokine or growth factor retains its biological activity while bound to the conjugate and may also be released by erosion of the polymer conjugate.

The conjugates of the invention, and compositions containing such conjugates, are useful in a wide range of therapeutic applications. For example, the conjugates are useful in dermal wound healing and cardiovascular applications where immunological reactions are to be minimized or blood coagulation is to be avoided. The conjugates may also be used in various ophthalmic applications, such as vitreous fluid replacement, corneal shields for delivery of drugs to the eye, or as lenticules. Other indications include use of the conjugates in orthopedic surgery or as joint lubricants in the treatment of arthritis. Other potential uses for the conjugates are as an injectable drug or cell delivery system, as a dermal would dressing, or as a coating for solid implants intended for long-term use in the body.

The conjugates can further be made into a variety of forms, including, but not limited to, membranes, beads, sponges, tubes, sheets, and formed implants. Formed implants can be used as prosthetic devices for replacement or augmentation of various organs and body parts such as heart valves, patellas, ears, noses, cheekbones, etc.

A primary feature of the invention is to provide biocompatible conjugates formed by covalently binding synthetic polymers such as activated polyethylene glycol to one or more species of glycosaminoglycan.

Another feature of the invention is to provide glycosaminoglycan-synthetic polymer conjugates which are further covalently bound to collagen.

Another feature of the invention is to provide pharmaceutically acceptable, nonimmunogenic compositions comprising pharmaceutically acceptable fluid carriers in which the conjugates are dispersed.

Another feature of the invention is to provide a method of tissue augmentation comprising forming biocompatible glycosaminoglycan-synthetic polymer conjugates, dehydrating the conjugates to form a solid, grinding the solid into particles, suspending the particles in a pharmaceutically acceptable nonaqueous fluid carrier, and injecting the suspension into the site of augmentation, after which the particles will rehydrate and expand in size.

An important advantage of the present invention is that the glycosaminoglycan-synthetic polymer conjugates have a greater degree of stability in vivo as compared with conventional glycosaminoglycan compositions.

Another feature of the invention is that the glycosaminoglycan-synthetic polymer conjugates can be formed using a range of different molecular weight synthetic polymers in order to adjust the physical characteristics of the composition.

Another advantage of the present invention is that the glycosaminoglycan-synthetic polymer conjugates have superior handling characteristics as compared with conventional glycosaminoglycan compositions.

Another advantage of the present invention is that the glycosaminoglycan-synthetic polymer conjugate compositions generate a decreased immune reaction as compared with conventional collagen compositions.

Another advantage of the present invention is that the glycosaminoglycan-synthetic polymer conjugate compositions have improved moldability, malleability, and elasticity as compared with conventional glycosaminoglycan compositions.

Other features of the present invention include the ability to formulate the compositions and conjugates in combination with pharmaceutically active proteins such as cytokines or growth factors in order to improve the activity and available half-life of such cytokines or growth factors under physiological conditions.

Another feature of the present invention is that the glycosaminoglycans or derivatives thereof may be bound to the synthetic polymer by means of a variety of types of covalent linkages including ester and ether linkages.

Another advantage of the present invention is that an ether linkage may be used to form the covalent bond to create the conjugate and this bond is resistant to hydrolysis.

Another advantage of the invention is that the three-part conjugates comprising covalently bonded glycosaminoglycan-synthetic polymer-collagen have different physical and chemical properties than either glycosaminoglycan-synthetic polymer conjugates or collagen-synthetic polymer conjugates alone, which properties can be manipulated as desired by varying the relative ratios of glycosaminoglycan and collagen in the composition.

These and other features of the present invention will become apparent to those skilled in the art upon reading the details of the structure, synthesis, and usage of the glycosaminoglycan-synthetic polymer conjugates set forth below.

DETAILED DESCRIPTION OF THE PREFERRED EMBODIMENTS OF THE INVENTION

It must be noted that, as used in this specification and the appended claims, the singular forms "a", "an", and "the" include plural referents unless the context clearly dictates otherwise. Thus, for example, reference to "a polymer" includes mixtures of such polymers, reference to "an attaching group or a linking group" includes one or more different types of groups known by those skilled in the an or capable of forming a covalent bond, and reference to "the synthetic polymer" includes mixtures of different types of synthetic polymers such as various activated polyethlene glycols and so forth.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, only the preferred methods and materials are described below; it is not inteneded that the invention be limited to these preferred embodiments, however.

All publications mentioned herein are incorporated herein by reference. Further, specific terminology of particular importance to the description of the present invention is defined below.

Definitions

The term "glycosaminoglycan" is intended to encompass complex polysaccharides which are not biologically active (i.e., not compounds such as ligands or proteins) having repeating units of either the same saccharide subunit or two different saccharide subunits. Some examples of glycosaminoglycans include dermatan sulfate, hyaluronic acid, the chondroitin sulfates, chitin, heparin, keratan sulfate, keratosulfate, and derivatives thereof. In general, the glycosaminoglycans are extracted from a natural source and purified and derivatized. However, they may be synthetically produced or synthesized by modified microorganisms such as bacteria.

The term "hyaluronic acid" is intended to encompass naturally occurring and synthetic forms of the polymer—$(C_8H_{13}O_4N)_n \cdot (C_6H_8O_5)_nO$—(n=1 to n=about 5,000), and derivatives thereof. Particularly preferred derivatives include those having functionalized moieties which allow chemical reaction with another molecule to form a covalent bond, such as deacetylated hyaluronic acid. The compound includes alternating units of 1,4-linked N-acetylglucosamine and glucuronic acid units. Hyaluronic acid is a viscous, high molecular weight mucopolysaccharide found in mammalian fluids and connective tissue. The formula for hyaluronic acid is shown below.

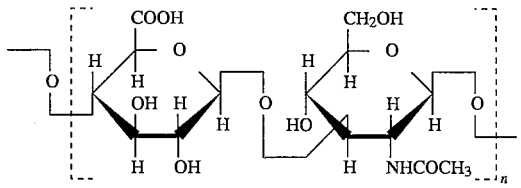

Alternating units of 1,4-linkled
N-acetylglucosamine and glucuronic acid wherein n ranges from 1 to about 5,000.

The term "chondroitin sulfate", as used herein, is intended to encompass three major compounds: chondroitin sulfate A, dermatan sulfate (also known as chondroitin sulfate B, which is an isomer of chondroitin sulfate A), and chondroitin sulfate C. The structures of these three compounds are shown below.

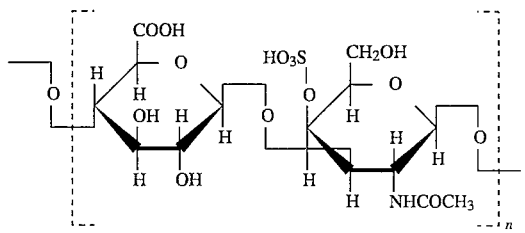

Repeating unit of chondroitin sulfate A wherein n ranges from about 10 to about 300;

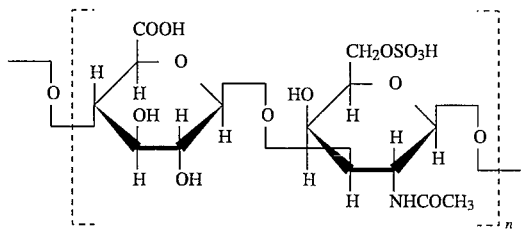

Repeating unit of chondroitin sulfate C wherein n ranges from about 20 to about 200;

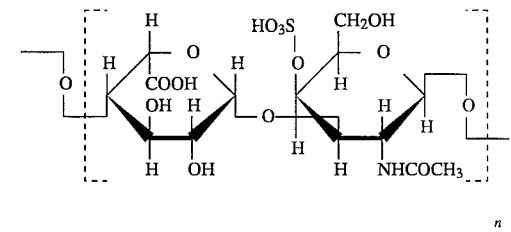

Repeating unit of dermatan sulfate
(chondroitin sulfate B)

wherein n ranges from about 10 to about 300.

The term "chitin" is intended to encompass polymers comprising repeating units of N-acetylglucosamine. The structure of chitin is shown below.

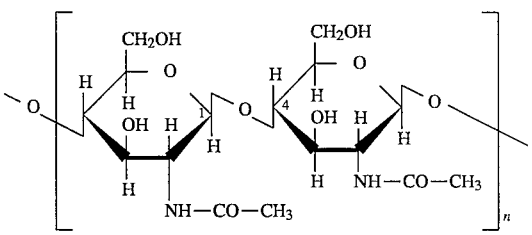

wherein n ranges from about 500 to about 2,000.

The term "chitosans" refers to both partially and fully deacetylated chitins. The term "chitosan 1" refers to partially deacetylated chitin, as shown below.

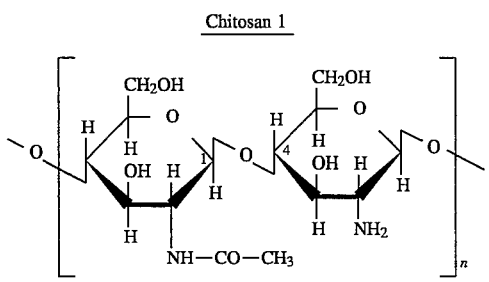

Chitosan 1

N-Acetylglucosamine (Partially deacetylated chitin)

wherein n ranges from about 500 to about 2,000.

The term "chitosan 2" refers to fully deacetylated chitin, as shown below.

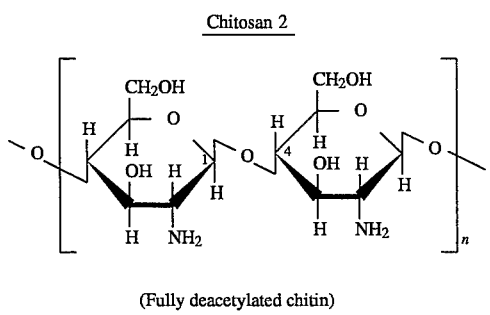

Chitosan 2

(Fully deacetylated chitin)

wherein n ranges from about 500 to about 2,000.

The term "keratan sulfate" refers to polymers having the repeating structure shown below.

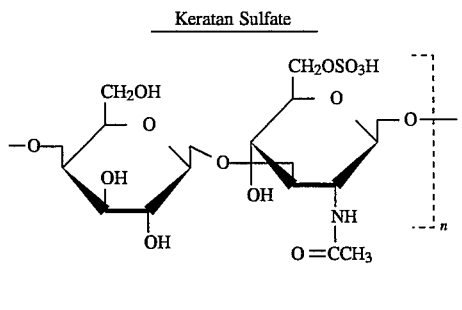

Keratan Sulfate

Repeating unit of keratan sulfate wherein n ranges from about 10 to about 100.

The term "keratosulfate" refers to a polymer that is an isomer of keratan sulfate, having the repeating structure shown below.

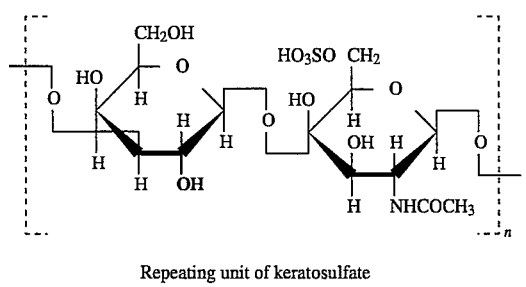

Keratosulfate

Repeating unit of keratosulfate wherein n ranges from about 10 to about 100.

The term "heparin" refers to polymers comprising alternating units of sulfated glucosamine and sulfated glucuronic acid, as shown below.

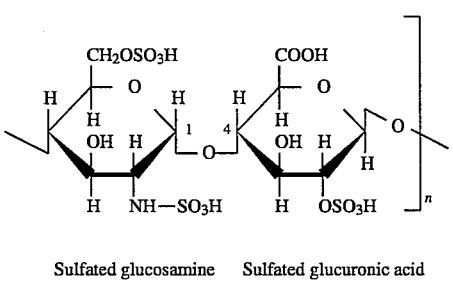

Heparin

Sulfated glucosamine   Sulfated glucuronic acid wherein n ranges from about 2 to about 3,000.

The terms "biologically inert polymers", "biocompatible polymers", and "biologically inert, biocompatible polymers" are used interchangeably herein. The terms refer to biologically inert, insoluble, biocompatible polymers and their derivatives which can be covalently bound to synthetic hydrophilic polymers to form the conjugates of the invention. These terms encompass polymers that are biologically inert, insoluble, nontoxic and do not generate any appreciable immune reaction when incorporated into a living being such as a human.

Preferred synthetic polymers for use in the present invention are hydrophilic and are highly pure or are purified to a highly pure state such that the polymer is or is treated to become pharmaceutically pure so that it may be injected into a human patient. Most hydrophilic synthetic polymers can be rendered water-soluble by incorporating a sufficient number of oxygen (or less frequently nitrogen) atoms available for forming hydrogen bonds in aqueous solutions. Preferred synthetic polymers are hydrophilic but not necessarily water-soluble. Hydrophilic synthetic polymers used herein include activated forms of polyethylene glycol (PEG), polyoxyethylene, polymethylene glycol, polytrimethylene glycols, polyvinylpyrrolidones, and derivatives thereof with activated PEG being particularly preferred. The synthetic polymers can be linear or multiply branched, but are typically not substantially crosslinked. Other suitable hydrophilic synthetic polymers include polyoxyethylene-polyoxypropylene block polymers and copolymers.

Polyoxyethylene-polyoxypropylene block polymers having an ethylene dime nucleus (and thus having four ends) are commercially available and may be used in the practice of the invention. Naturally occurring polymers such as proteins, starch, cellulose, heparin, hyaluronic acid and derivatives thereof and the like are expressly excluded from the scope of this definition. All suitable synthetic polymers will be non-toxic, non-inflammatory, and nonimmunogenic when administered subcutaneously, and will preferably be essentially nondegradable in vivo over a period of at least several months. The hydrophilic synthetic polymer may increase the hydrophilicity of the conjugate, but does not render it water-soluble. The most preferred hydrophilic synthetic polymers include mono-, di-, and multifunctionally activated polyethylene glycols. Monofunctionally activated PEG has only one reactive hydroxy group, while difunctionally activated PEG has reactive groups at each end. Monofunctionally activated PEG preferably has an average molecular weight between about 100 and about 15,000, more preferably between about 200 and about 8,000, and most preferably about 5,000. Difunctionally activated PEG preferably has an average molecular weight of about 400 to about 40,000, more preferably between about 3,000 to about 10,000. Multifunctionally activated PEG preferably has an average molecular weight between about 3,000 and 100,000.

PEG can be rendered monofunctionally activated by forming an alkylene ether group at one end. The alkylene ether group may be any suitable alkoxy radical having 1–6 carbon atoms, for example, methoxy, ethoxy, propoxy, 2-propoxy, butoxy, hexyloxy, and the like. Methoxy is presently preferred. Difunctionally activated PEG is provided by allowing a reactive hydroxy group at each end of the linear molecule. The reactive groups are preferably at the ends of the polymer, but may be provided along the length thereof. Multifunctionally activated synthetic polymers are capable of crosslinking the compositions of the invention, and may be used to attach cytokines or growth factors to the glycosaminoglycan-synthetic polymer conjugate.

The term "nonimmunogenic" refers to molecules and compositions which produce no appreciable immunogenic or allergic reaction when injected or otherwise implanted into the body of a human subject.

The term "chemically conjugated" as used herein means attached through a covalent chemical bond. In the practice of the invention, a hydrophilic synthetic polymer and a glycosaminoglycan or derivative thereof may be chemically conjugated by using a linking radical, so that the hydrophilic synthetic polymer and glycosaminoglycan are each bound to the radical, but not directly to each other. The term "biocompatible conjugate" refers to a biologically inert, biocompatible polymer chemically conjugated to a hydrophilic synthetic polymer, within the meaning of this invention. For example,"PEG-hyaluronic acid" denotes a composition of the invention wherein hyaluronic acid is chemically conjugated to PEG. The hydrophilic synthetic polymer may be "chemically conjugated" to the glycosaminoglycan such as hyaluronic acid by means of a number of different types of chemical linkages. For example, the conjugation can be via an ester or a urethane linkage, but is more preferably by means of an ether linkage. An ether linkage is preferred in that it can be formed without the use of toxic chemicals and is not readily susceptible to hydrolysis in vivo.

Those of ordinary skill in the art will appreciate that hydrophilic synthetic polymers such as polyethylene glycol cannot be prepared practically to have exact molecular weights, and that the term "molecular weight" as used herein refers to the average molecular weight of a number of molecules in any given sample, as commonly used in the art. Thus, a sample of PEG 2,000 might contain a statistical mixture of polymer molecules ranging in weight from, for example, 1,500 to 2,500, with one molecule differing slightly from the next over a range. Specification of a range of molecular weight indicates that the avenge molecular weight may be any value between the limits specified, and may include molecules outside those limits. Thus, a molecular weight range of about 800 to about 20,000 indicates an average molecular weight of at least about 800, ranging up to about 20,000.

The term "available lysine residue" as used herein refers to lysine side chains exposed on the outer surface of natural polymer molecules, which are positioned in a manner to allow reaction with activated PEG. The number of available lysine residues may be determined by reaction with sodium 2,4,6-trinitrobenzenesulfonate (TNBS).

The terms "treat" and "treatment" as used herein refer to augmentation, repair, prevention, or alleviation of defects, particularly defects due to loss or absence of soft tissue or soft tissue support, or to loss or absence of bone. Additionally, "treat" and "treatment" also refer to the prevention, maintenance, or alleviation of disorders or disease using a biologically active protein coupled to a conjugate-containing composition of the invention. Accordingly, treatment of soft tissue includes augmentation of soft tissue, for example, implantation of conjugates of the invention to restore normal or desirable dermal contours, as in the removal of dermal creases or furrows, or as in the replacement of subcutaneous fit in maxillary areas where the fat is lost due to aging, or in the augmentation of submucosal tissue, such as the urinary or lower esophageal sphincters. Treatment of bone and cartilage includes the use of biocompatible conjugates, particularly in combination with suitable particulate materials, to replace or repair bone tissue, for example, in the treatment of bone nonunions or fractures. Treatment of bone also includes use of conjugate-containing compositions, with or without additional bone growth factors. Compositions comprising conjugates with ceramic particles, preferably hydroxyapatite and/or tricalcium phosphate, are particularly useful for the repair of stress-bearing bone due to its high tensile strength.

The terms "cytokine" and "growth factor" are used to describe biologically active molecules and active peptides (which may be either naturally occurring or synthetic) which aid in healing or regrowth of normal tissue including growth factors and active peptides. The function of cytokines is two-fold: 1) they can incite local cells to produce new collagen or tissue, or 2) they can attract cells to the site in need of correction. As such, cytokines and growth factors serve to encourage "biological anchoring" of the implant within the host tissue. As previously described, the cytokines can either be admixed with the conjugate or chemically coupled to the conjugate. For example, one may incorporate cytokines such as interferons (IFN), tumor necrosis factors (TNF), interleukins, colony stimulating factors (CSFs), or growth factors such as osteogenic factor extract (OFE), epidermal growth factor (EGF), transforming growth factor (TGF) alpha, TGF-$\beta$ (including any combination of TGF-$\beta$s), TGF-$\beta$1, TGF-$\beta$2, platelet derived growth factor (PDGF-AA, PDGF-AB, PDGF-BB), acidic fibroblast growth factor (FGF), basic FGF, connective tissue activating peptides (CTAP), $\beta$-thromboglobulin, insulin-like growth factors, erythropoietin (EPO), nerve growth factor (NGF), bone morphogenic protein (BMP), osteogenic factors, and the like. Incorporation of such cytokines, and appropriate combinations of cytokines and growth factors can facilitate the regrowth and remodeling of the implant into normal tissue, or may be used in the treatment of wounds. Further, one may chemically link the cytokines or growth factors to the glycosaminoglycan-synthetic polymer conjugate by employing a suitable amount of multifunctionally activated synthetic polymer molecules during synthesis. The cytokines or growth factors may then be attached to the functional sites of the multifunctionally activated synthetic polymers by the same method used to attach activated PEG to glycosaminoglycans, or by any other suitable method. By tethering cytokine or growth factor molecules to the implant, the amount of cytokines or growth factor required to be therapeutically effective is substantially reduced. Conjugates incorporated with cytokines or growth factors may serve as effective controlled release drug delivery means. By varying the chemical linkage between the glycosaminoglycan and the synthetic polymer, it is possible to vary the effect with respect to the release of the cytokine or growth factor. For example, when an "ester" linkage is used, the linkage is more easily broken under physiological conditions, allowing for sustained release of the growth factor or cytokine from the matrix. However, when an "ether" linkage is used, the bonds are not easily broken and the cytokine or growth factor will remain in place for longer periods of time with its active sites exposed, providing a biological effect on the natural substrate for the active site of the protein. It is possible to include a mixture of conjugates with different linkages so as to obtain variations in the effect with respect to the release of the cytokine or growth factor, i.e., the sustained release effect can be modified to obtain the desired rate of release.

The term "effective amount" refers to the amount of composition required in order to obtain the effect desired. Thus, a "tissue growth-promoting amount" of a composition containing a cytokine or growth factor refers to the amount of cytokine or growth factor needed in order to stimulate tissue growth to a detectable degree. Tissue, in this context, includes connective tissue, bone, cartilage, epidermis and dermis, blood, and other tissues. The actual mount which is determined to be an effective mount will vary depending on factors such as the size, condition, sex and age of the patient and can be more readily determined by the caregiver.

The term "sufficient mount" as used herein is applied to the amount of carder used in combination with the conjugates of the invention. A sufficient mount is that mount which, when mixed with the conjugate, renders it in the physical form desired, for example, injectable solution, injectable suspension, plastic or malleable implant, rigid stress-bearing implant, and so forth. Injectable formulations generally include an amount of fluid carrier sufficient to render the composition smoothly injectable, whereas malleable implants have substantially less carrier and have a clay-like consistency. Rigid stress-bearing implants may include no carrier at all and have a high degree of structural integrity. The amount of the carrier can be varied and adjusted depending on the particular conjugate used and the end result desired. Such adjustments will be apparent to those skilled in the art upon reading this disclosure.

The term "suitable particulate material" as used herein refers to a particulate material which is substantially insoluble in water, nonimmunogenic, biocompatible, and immiscible with collagen-polymer conjugate. The particles of material may be fibrillar, or may range in size from about 20 to 250 μm in diameter and be bead-like or irregular in shape. Exemplary particulate materials include without limitation fibrillar crosslinked collagen, gelatin beads, crosslinked collagen-dPEG particles, polytetrafluoroethylene beads, silicone rubber beads, hydrogel beads, silicon carbide beads, and glass beads. Preferred particulate materials are calcium phosphates, most preferably hydroxyapatite and/or tricalcium phosphate particles.

The term "solid implant" refers to any solid object which is designed for insertion and use within the body, and includes bone and cartilage implants (e.g., artificial joints, retaining pins, cranial plates, and the like, of metal, plastic and/or other materials), breast implants (e.g., silicone gel envelopes, foam forms, and the like), catheters and cannulas intended for long-term use (beyond about three days), artificial organs and vessels (e.g., artificial hearts, pancreases, kidneys, blood vessels, and the like), drug delivery devices (including monolithic implants, pumps and controlled release devices such as Alzet® minipumps, steroid pellets for anabolic growth or contraception, and the like), sutures for dermal or internal use, periodontal membranes, lenticules, corneal shields, platinum wires for aneurysm treatment, and the like.

The term "suitable fibrous material", as used herein, refers to a fibrous material which is substantially insoluble in water, nonimmunogenic, biocompatible, and immiscible with the biocompatible conjugate of the invention. The fibrous material may comprise a variety of materials having these characteristics and are combined with compositions of the conjugate in order to form and/or provide structural integrity to various implants or devices used in connection with medical and pharmaceutical uses. For example, the conjugate compositions of the invention can be coated on the "suitable fibrous material" which can then be wrapped around a bone to provide structural integrity to the bone. Thus, the "suitable fibrous material" is useful in forming the "solid implants" of the invention.

The term "in situ" as used herein means at the site of administration. Thus, the injectable reaction mixture compositions are injected or otherwise applied to a site in need of augmentation, and allowed to crosslink at the site of injection. Suitable sites will generally be intradermal or subcutaneous regions for augmenting dermal support, at the site of bone fractures for wound healing and bone repair, and within sphincter tissue for sphincter augmentation (e.g., for restoration of continence).

The term "aqueous mixture" includes liquid solutions, suspensions, dispersions, colloids, and the like containing a natural polymer and water.

The term "collagen" is used in its conventional sense to describe a material which is the major protein component of the extracellular matrix of bone, cartilage, skin, and connective tissue in animals and derivatives. Collagen in its native form is typically a rigid, rod-shaped molecule approximately 300 nm long and 1.5 nm in diameter. It is composed of three collagen polypeptides which form a tight triple helix. The collagen polypeptides are characterized by a long midsection having the repeating sequence -Gly-X-Y-, where X and Y are often proline or hydroxyproline, bounded at each end by the "telopeptide" regions, which constitute less than about 5% of the molecule. The telopeptide regions of the collagen chains are typically responsible for the crosslinking between chains, and for the immunogenicity of the protein. Collagen occurs in several "types", having differing physical properties. The most abundant types are Types I–III. The present disclosure includes these and other known types of collagen including natural collagen and collagen which is processed or modified, i.e., various collagen derivatives. Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

The term "dehydrated" means the material is air-dried or lyophilized to remove substantially all unbound water.

General Method

To form the conjugates of the invention, glycosaminoglycans are, in general, chemically derivatized and then covalently bound to a functionally activated hydrophilic synthetic polymer. This can be carried out using a number of suitable methods. In accordance with one method, (1) the hydrophilic synthetic polymer is activated, (2) the glycosaminoglycan is subjected to chemical modification by deacetylation and/or desulfation, and (3) the activated synthetic polymer is reacted with the chemically modified glycosaminoglycan.

Activation of Polyethylene Glycol (PEG)

The first step in forming the conjugates of the invention generally involves functionalization, or activation, of the synthetic hydrophilic polymer. Although different synthetic hydrophilic polymers can be used in connection with forming the conjugate, the polymer must be biocompatible, hydrophilic, but relatively insoluble, and is preferably one or more forms of derivatized polyethylene glycol (PEG), due to its known biocompatibility. Various forms of derivatized PEG are extensively used in the modification of biologically active molecules because PEG can be formulated to have a wide range of solubilities and because it lacks toxicity, antigenicity, immunogenicity, and does not typically interfere with the enzymatic activities and/or conformations of peptides. Furthermore, PEG is generally non-biodegradable and is easily excreted from most living organisms including humans.

Various functionalized polyethylene glycols have been used effectively in fields such as protein modification (see Abuchowski et al., *Enzymes as Drugs*, John Wiley & Sons: New York, N.Y. (1981) pp. 367–383; and Dreborg et al., *Crit. Rev. Therap. Drug Carrier Syst.* (1990) 6:315), peptide chemistry (see Mutter et al., *The Peptides*, Academic: New York, N.Y. 2:285–332; and Zalipsky et al., *Int. J. Peptide Protein Res.* (1987) 30:740), and the synthesis of polymeric drugs (see Zalipsky et al., *Eur. Polym. J.* (1983) 19:1177; and Ouchi et al., *J. Macromol. Sci.-Chem.* (1987) A24:1011). Various types of conjugates formed by the binding of activated (functionalized) polyethylene glycol with specific pharmaceutically active proteins have been disclosed and found to have useful medical applications in part due to the stability of such conjugates with respect to proteolytic digestion, reduced immunogenicity, and longer half-lives within living organisms.

One form of polyethylene glycol which has been found to be particularly useful is monomethoxy-polyethylene glycol (mPEG), which can be activated by the addition of a compound such as cyanuric chloride, then coupled to a protein (see Abuchowski et al., *J. Biol. Chem.* (1977) 252:3578). Although such methods of activating polyethylene glycol can be used in connection with the present invention, they are not particularly desirable in that the cyanuric chloride is relatively toxic and must be completely removed from any resulting product in order to provide a pharmaceutically acceptable composition.

Activated forms of PEG, including activated forms of mPEG, can be made from reactants which can be purchased commercially. One form of activated PEG which has been found to be particularly useful in connection with the present invention is mPEG-succinate-N-hydroxysuccinimide ester (SS-PEG) (see Abuchowski et al., *Cancer Biochem. Biphys.* (1984) 7:175). Activated forms of PEG such as SS-PEG react with the proteins under relatively mild conditions and produce conjugates without destroying the specific biological activity and specificity of the protein attached to the PEG. However, when such activated PEGs are reacted with proteins, they react and form linkages by means of ester bonds. Although ester linkages can be used in connection with the present invention, they are not particularly preferred in that they undergo hydrolysis when subjected to physiological conditions over extended periods of time (see Dreborg et al., *Crit. Rev. Therap. Drug Carrier Syst.* (1990) 6:315; and Ulbrich et al., *J. Makromol. Chem.* (1986) 187:1131).

It is possible to link PEG to proteins via urethane linkages, thereby providing a more stable attachment which is more resistant to hydrolytic digestion than the ester linkages (see Zalipsky et al., Polymeric Drug and Drug Delivery Systems, Chapter 10, "Succinimidyl Carbonates of Polyethylene Glycol" (1991)). The stability of urethane linkages has been demonstrated under physiological conditions (see Veronese et al., *Appl. Biochem. Biotechnol.* (1985) 11:141; and Larwood et al., *J. Labelled Compounds Radiopharm.* (1984) 21:603). Another means of attaching the PEG to a protein can be by means of a carbamate linkage (see Beauchamp et al., *Anal. Biochem.* (1983) 131:25; and Berger et al., *Blood* (1988) 71:1641). The carbamate linkage is created by the use of carbonyldiimidazole-activated PEG. Although such linkages have advantages, the reactions are relatively slow and may take 2 to 3 days to complete.

The various means of activating PEG described above and publications cited in connection with the activation means are described in connection with linking the PEG to specific biologically active proteins and not inert, biologically inactive, natural polymers. (See *Polymeric Drug and Drug Delivery Systems,* Chapter 10, "Succinimidyl Carbonates of Polyethylene Glycol" (1991 ).) However, the present invention now discloses that such activated PEG compounds can be used in connection with the formation of inert, biocompatible conjugates. Such conjugates provide a range of improved, unexpected characteristics and as such can be used to form the various compositions of the present invention.

Specific Forms of Activated PEG

For use in the present invention, polyethylene glycol is modified in order to provide activated groups on one or, preferably, two or more ends of the molecule so that covalent binding can occur between the PEG and the free amino groups on the chemically derivatized glycosaminoglycan. Some specific activated forms of PEG are shown structurally below, as are generalized reaction products obtained by reacting activated forms of PEG with derivatized glycosaminoglycans. In Formulas 1–7, the term GAG-PLYM is used to represent chemically derivatized glycosaminoglycan polymers.

The first activated PEG is difunctionally activated PEG succinimidyl glutarate, referred to herein as (SG-PEG). The structural formula of this molecule and the reaction product obtained by reacting it with a glycosaminoglycan derivative are shown in Formula 1.

conjugate formed by reacting the activated PEG with a glycosaminoglycan derivative.

FORMULA 1

S-PEG: Difunctionally Activated PEG Succinimidyl Glutarate

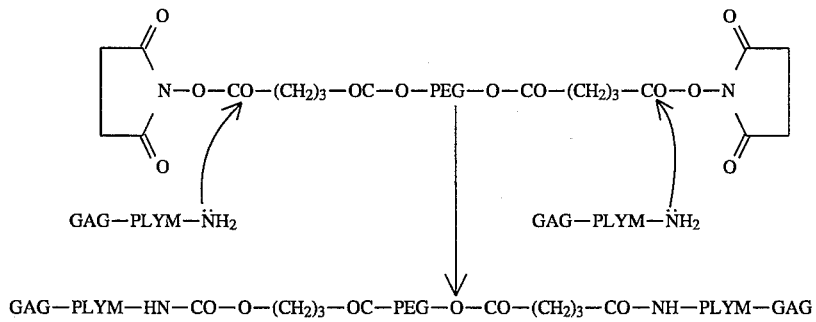

GAG—PLYM—HN—CO—O—(CH$_2$)$_3$—OC—PEG—O—CO—(CH$_2$)$_3$—CO—NH—PLYM—GAG

Another difunctionally activated form of PEG is referred to as PEG succinimidyl (S-PEG). The structural formula for this compound and the reaction product obtained by reacting it with a glycosaminoglycan derivative such as deacetylated hyaluronic acid is shown in Formula 2. In any general structural formula for the compounds, the subscript 3 is replaced with an "n". In the embodiment shown in Formula 1, n=3, in that there are three repeating CH$_2$ groups on either side of the PEG. The structure in Formula 2 results in a conjugate which includes an "ether" linkage which is not subject to hydrolysis. This is distinct from the conjugate shown in Formula 1, wherein an ester linkage is provided. The ester linkage is subject to hydrolysis under physiological conditions.

FORMULA 2

S-PEG, n = 3: Difunctionally Activated PEG Succinimidyl

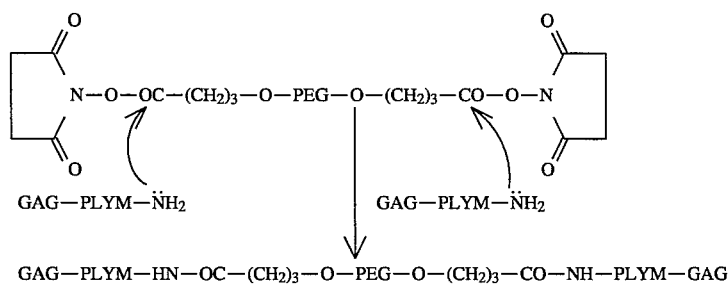

GAG—PLYM—HN—OC—(CH$_2$)$_3$—O—PEG—O—(CH$_2$)$_3$—CO—NH—PLYM—GAG

Yet another difunctionally activated form of polyethylene glycol, wherein n=2, is shown in Formula 3, as is the

FORMULA 3

S-PEG, n = 2: Difunctionally Activated PEG Succinimidyl

-continued
FORMULA 3

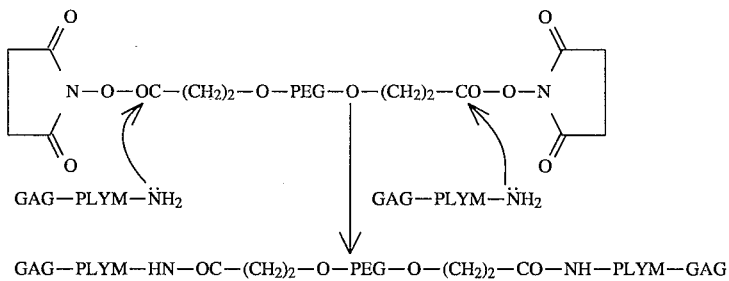

Another preferred embodiment of the invention similar to the compounds of Formulas 2 and 3 is provided when n=1. The structural formula and resulting conjugate are shown in Formula 4. It is noted that the conjugate includes both an ether and a peptide linkage. These linkages are stable under physiological conditions.

FORMULA 4

S-PEG, n = 1: Difunctionally Activated PEG Succinimidyl

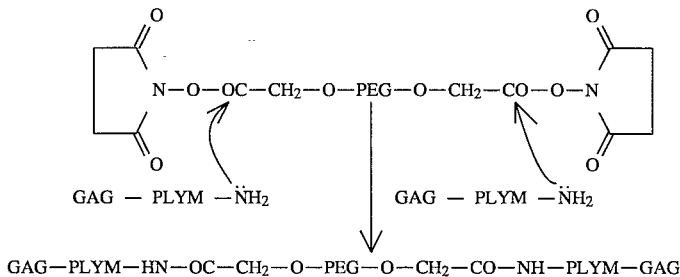

Yet another difunctionally activated form of PEG is provided when n=0. This compound is referred to as PEG succmimidyl carbonate (SC-PEG). The structural formula of this compound and the conjugate formed by reacting SC-PEG with a glycosaminoglycan derivative is shown in Formula 5.

FORMULA 5

SC-PEG, n = 0: Difunctionally Activated PEG Succinimidyl Carbonate

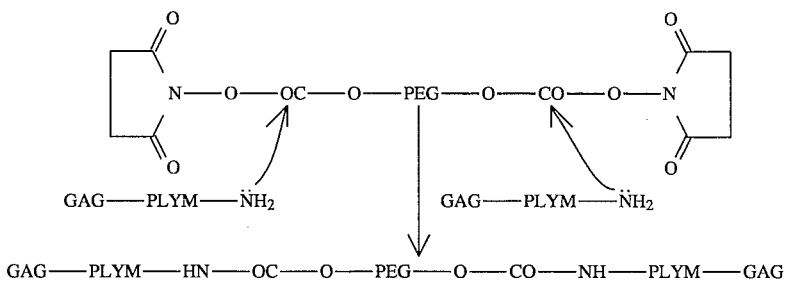

All of the derivatives depicted in Formulas 1–5 involve the inclusion of the succinimidyl group. However, different activating groups can be attached to one or both ends of the PEG molecule. For example, PEG can be derivatized to form difunctionally activated PEG propion aldehyde (A-PEG), which is shown in Formula 6, as is the conjugate formed by the reaction of A-PEG with a glycosaminoglycan derivative. The linkage shown in Formula 6 is referred to as a $—(CH_2)_n—NH—$ linkage, where n=1–10.

FORMULA 6

A-PEG: Difunctionally Activated PEG Propion Aldehyde

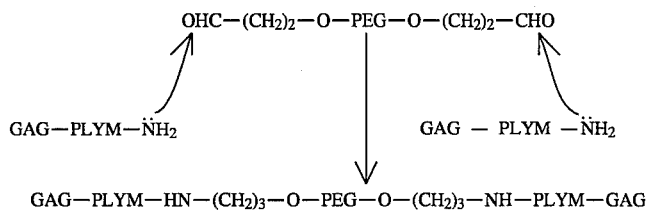

GAG—PLYM—HN—(CH$_2$)$_3$—O—PEG—O—(CH$_2$)$_3$—NH—PLYM—GAG

Yet another difunctionally activated form of polyethylene glycol is PEG glycidyl ether (E-PEG), which is shown in Formula 7, as is the conjugate formed by reacting such with a glycosaminoglycan derivative.

FORMULA 7

E-PEG: Difunctionally Activated PEG Glycidyl Ether

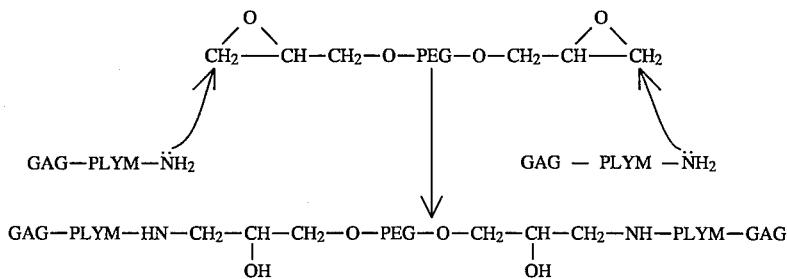

GAG—PLYM—HN—CH$_2$—CH—CH$_2$—O—PEG—O—CH$_2$—CH—CH$_2$—NH—PLYM—GAG
                                     OH                                         OH

Chemical Derivatization of Glycosaminoglycans

To make the glycosaminoglycan-polymer conjugates of the present invention, the glycosaminoglycan first must be chemically derivatized in a manner that will provide free amino (—NH$_2$) groups which are available for covalent crosslinking with PEG. Chemical derivatization of the glycosaminoglycan to provide free amino groups can be accomplished by either deacetylation of desulfation, both of which may be effected by the addition of a strong base such as sodium hydroxide to the glycosaminoglycan solution.

Glycosaminoglycans such as hyaluronic acid, the chondroitin sulfates, keratan sulfate, keratosulfate, and chitin can be deacetylated (removal of the —COCH$_3$ group) to provide free amino groups, as shown in Reaction Schemes 1 and 2 for hyaluronic acid and chitin, respectively.

Reaction Scheme 1

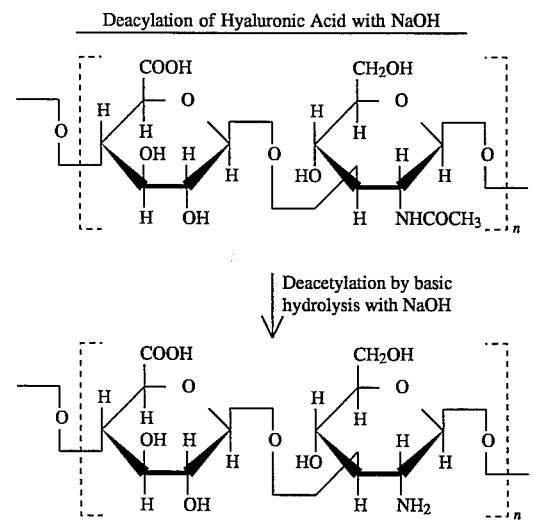

Reaction Scheme 2
Deacetylation of Chitin with NaOH

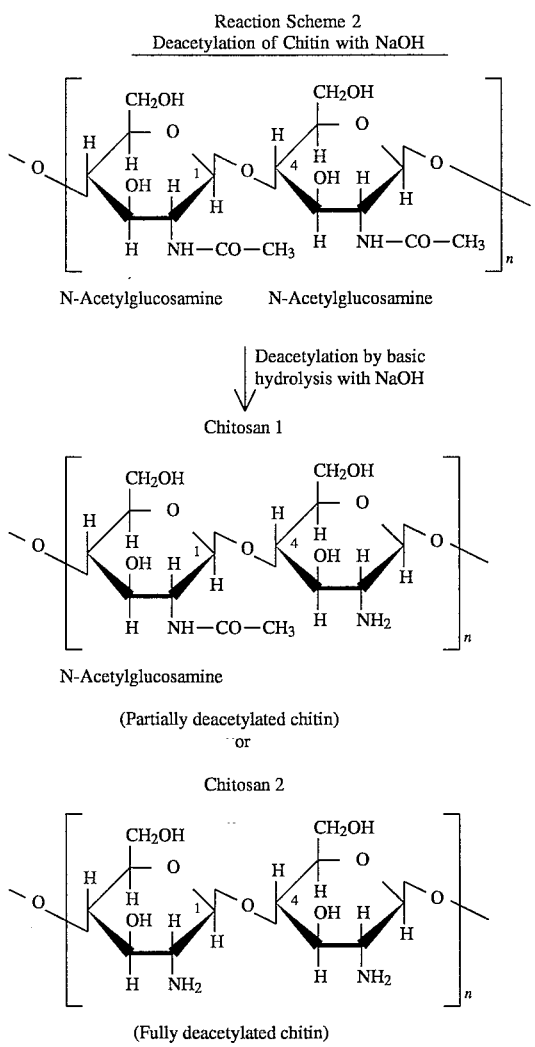

N-Acetylglucosamine (Partially deacetylated chitin)
or
Chitosan 2

(Fully deacetylated chitin)

Glycosaminoglycans such as heparin, the chondroitin sulfates, keratan sulfate, and keratosulfate can be desulfated (removal of the —$SO_3$ group) to provide free amino groups, as shown in Reaction Scheme 3.

Reaction Scheme 3
Desulfation of Heparin with NaOH

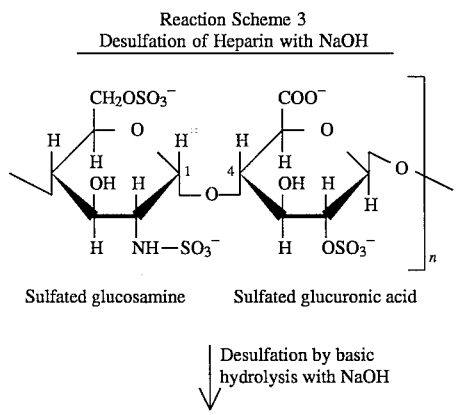

Sulfated glucosamine    Sulfated glucuronic acid

Desulfation by basic hydrolysis with NaOH

-continued
Reaction Scheme 3
Desulfation of Heparin with NaOH

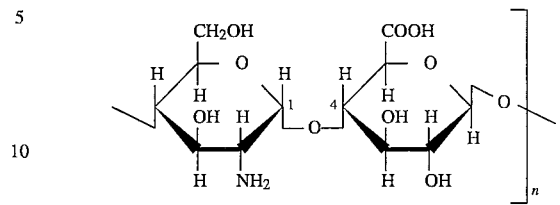

As per Table 1, below, certain glycosaminoglycans, such as the chondroitin sulfates, keratan sulfate, and keratosulfate contain both —$COCH_3$ and —$SO_3$ groups and are therefore subject to both deacetylation and desulfation by the addition of sodium hydroxide. Deacetylation and desulfation of chondroitin sulfate C is shown in Reaction Scheme 4.

TABLE 1

Derivatization of Glycosaminoglycans by Deacetylation and Desulfation

| Compound | Deacetylation | Desulfation |
|---|---|---|
| Chitin | Yes | No |
| Chondroitin sulfate A | Yes | Yes |
| Chondroitin sulfate B | Yes | Yes |
| Chondroitin sulfate C | Yes | Yes |
| Heparin | No | Yes |
| Hyaluronic acid | Yes | No |
| Keratan sulfate | Yes | Yes |
| Keratosulfate | Yes | Yes |

Crosslinking of Chemically Derivatized Glycosaminoglycans with PEG

Glycosaminoglycans that have been chemically derivatized to have free amino groups can be crosslinked with activated multifunctional PEG, as shown in Reaction Scheme 5 for deacetylated hyaluronic acid.

Glycosaminoglycan-polymer conjugates are formed within minutes of combining the chemically derivatized glycosaminoglycan and the functionally activated polymer. The glycosaminoglycan derivative can be mixed with the polymer using syringe-to-syringe mixing. Alternatively, the glycosaminoglycan derivative can be extruded into a solution of the activated polymer, crosslinking will occur as the polymer diffuses into the glycosaminoglycan. +p The rate of conjugate formation and the characteristics of the resulting conjugate can be varied by varying the type of activated PEG used and/or the molecular weight and concentration of the PEG. In general, the use of PEG species (such as S-PEG) which result in ether or urethane linkages lead to the creation of more stable conjugates than those which result in the readily hydrolyzed ester linkages. However, in certain situations, such as drug delivery applications, it is desirable to include the weaker ester linkages: the linkages are gradually broken by hydrolysis under physiological conditions, breaking apart the matrix and releasing the pharmaceutically active component held therein. Different species of PEG can be mixed and used in the same drug delivery composition, resulting in a varied rate of matrix degradation and, hence, drug release. +p Multifunctionally activated PEG can be used to crosslink more than one species of glycosaminoglycan derivative, or glycosaminoglycan derivatives and collagen, as shown in Reaction Scheme +b 6 for deacetylated hyaluronic acid and collagen. The resulting composite material has different physical and chemical properties than either PEG-crosslinked collagen or PEG-crosslinked glycosaminoglycan alone.

tation or sphincter augmentation) and drug delivery. For injectable formulations, glycosaminoglycan concentrations within the range of about 10 to about 100 mg/mL are generally used. The concentration of activated synthetic polymer in the composition is preferably within the range of about 1 to about 400 milligrams of activated synthetic polymer per millileter of composition.

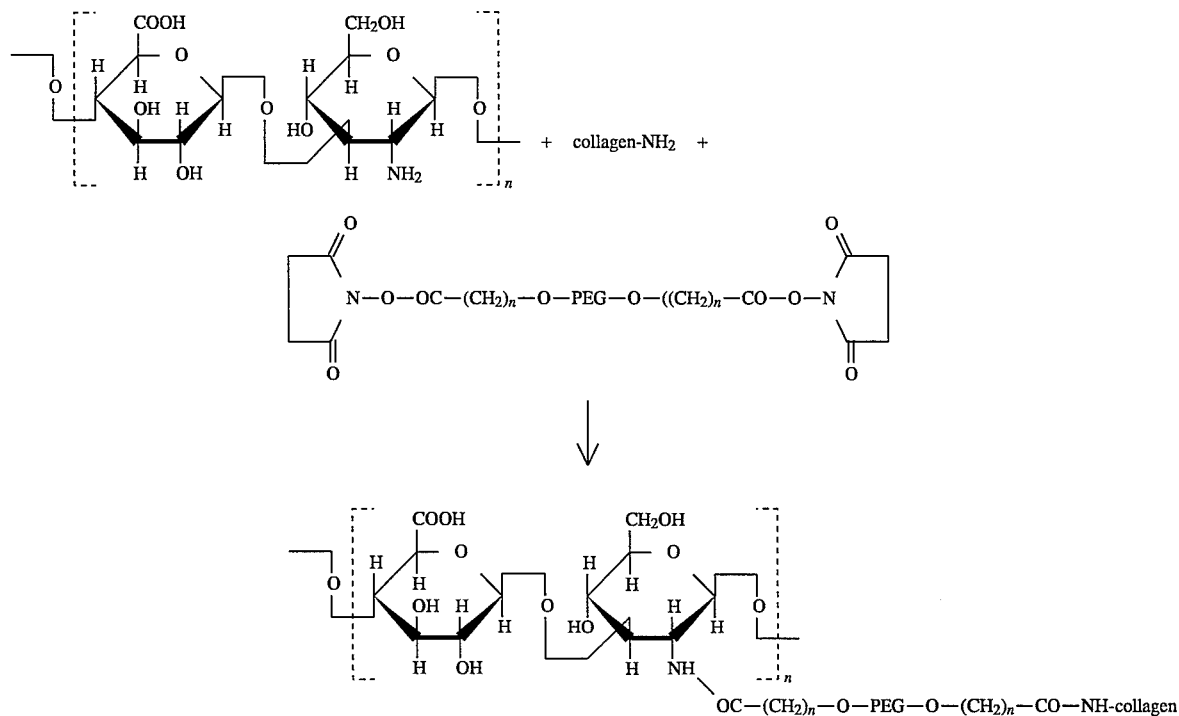

The glycosaminoglycan-polymer-collagen composites can be produced in a number of ways, as described in experimental Examples 3–6.

Suitable collagens for use in the invention include all types of collagen; however, types I, II, and III are preferred. The collagen used in the practice of the invention may be either fibrillar (e.g., Zyderm® Collagen) or nonfibrillar. Either atelopeptide or telopeptide-containing collagen may be used, depending on the desired end use of the conjugate. Various forms of collagen are available commercially, or may be prepared by the processes described in, for example, U.S. Pat. Nos. 3,949,073; 4,488,911; 4,424,208; 4,582,640; 4,642,117; 4,557,764; and 4,689,399, all incorporated herein by reference.

Collagen contains a number of available amino and hydroxy groups which may be used to bind the collagen to the glycosaminoglycan-synthetic polymer conjugate. Methods of conjugating collagen to polyethylene glycol are discussed in detail in U.S. Pat. No. 5,162,430.

Use and Administration

The primary use of the glycosaminoglycan-synthetic polymer and glycosaminoglycan-synthetic polymer-collagen conjugates of the invention is as injectable compositions for soft tissue augmentation (such as dermal augmen- Crosslinking between the glycosaminoglycan and the synthetic polymer can be performed in vitro, or a reaction mixture may be injected for crosslinking in situ. The glycosaminoglycan derivative and activated polymer can be stored in separate barrels of a double-barreled syringe. As the plunger of the syringe is depressed and the material is injected beneath the skin, the components mix in the needle of syringe and crosslink in situ. Some of the activated polymer molecules may additionally crosslink to the patient's own collagen to anchor the implant in place. Gel formation will occur within twenty minutes or less of administration. Injectable compositions may further be used for hard tissue repair in situations where surgery is not desirable or recommended. In hard tissue applications, the injectable composition serves as a matrix for regeneration of bone or cartilage at the site of placement.

In addition to aqueous injectable solutions, prepolymerized glycosaminoglycan-polymer conjugates can be dried and then ground into dried particulates. Alternatively, glycosaminoglycan-polymer conjugates can be dried in bead or droplet form. The beads or particles comprising the conjugates can be suspended in a nonaqueous carrier and injected to a soft tissue site in need of augmentation. Once in situ, the particulates rehydrate and swell three- to five-fold due to the hydrophilicity of the polyethylene glycol molecules. Less volume of product is therefore required to achieve the desired connection.

The multifunctionally activated synthetic polymers may be used to covalently crosslink glycosaminoglycan derivatives to collagen or to biologically active proteins such as cytokines and growth factors. Such compositions are particularly suited for use in wound healing, osteogenesis, and immune modulation. Tethering of biologically active molecules to glycosaminoglycans provides an effective sustained release drug delivery system. As described above, different species of polyethylene glycol can be included in the formulation to result in varying rates of drug release.

Compositions of the invention containing biologically active cytokines or growth factors such as TGF-β are prepared by admixing an appropriate amount of the cytokine or growth factor into the composition, or by incorporating the cytokine or growth factor into the glycosaminoglycan prior to treatment with activated PEG. Preferably, the cytokine or growth factor is first reacted with a molar excess of a multifunctionally activated polyethylene glycol in a dilute solution for three to four minutes. The cytokine or growth factor is preferably provided at a concentration of about 1 μg/mL to about 5 mg/mL, while the activated polymer is preferably added to a final concentration providing a thirty- to fifty-fold molar excess. The conjugated biologically active factor-synthetic polymer is then added to an aqueous glycosaminoglycan mixture (preferably having a concentration within the range of about 1 to about 60 mg/mL) at neutral pH (approximately 7–8) and allowed to react further to form biologically active factor-synthetic polymer-glycosaminoglycan conjugates. The resulting composition is allowed to stand overnight at ambient temperature. The pellet is collected by centrifugation and washed with PBS, using vigorous vortexing to remove unbound factor.

Compositions of the invention containing biologically active factors such as cytokines or growth factors are particularly suited for sustained release of factors, as in the case of wound healing promotion. Osteoinductive factors and cofactors (including TGF-β) and bone morphogenic protein (BMP) may advantageously be incorporated into compositions for bone replacement, augmentation, and/or defect repair. Alternatively, one may administer antiviral and antitumor factors such as TNF, interferons, CSFs, TGF-β, and the like for their pharmaceutical activities. The amount of cytokine or growth factor incorporated into the composition is determined based on the type of factor being used, the severity of the condition being treated, the rate of delivery desired, etc. These parameters may be determined by routine experimentation; for example, by preparing a conjugated factor-polymer-glycosaminoglycan composition as described above and assaying the release rate of factor in a suitable animal model.

Compositions of glycosaminoglycan-synthetic polymer conjugates can also be formed into relatively solid implants. Compositions of the invention can be prepared in a form that is dense and rigid enough to substitute for cartilage. These compositions are useful for repairing and supporting tissues which require some degree of structure and rigidity, for example, in reconstruction of the nose, ear, knee, larynx, tracheal rings, and joint surfaces. One can also replace tendons, ligaments, and blood vessels using appropriately formed cartilaginoid materials. In these applications, the material is generally cast or molded into the desired shape. Materials for tendon and ligament replacement may be formed by braiding or weaving filaments of the glycosaminoglycan—polymer conjugates into cords or ropes. In the case of artificial blood vessels, it may be advantageous to incorporate a reinforcing mesh (e.g., nylon, Teflon®, or Dacron®).

Formulations suitable for repair of bone defects or nonunions may be prepared by providing high concentration compositions of biocompatible conjugates, such as glycosaminoglycan-synthetic polymer; glycosaminoglycon-synthetic polymer-collagen; or one of these conjugates in combination with a cytokine or growth factor, any of which may be used in admixture with suitable particulate materials. When making bone repair compositions intended to persist for long periods of time invivo, the linkage between the glycosaminoglycan and synthetic polymer may be an ether linkage in order to avoid deterioration due to the hydrolysis of the ester linkages. Such conjugate/particulate compositions may be malleable or rigid, depending on the amount of liquid incorporated. Formulations for treatment of stress-bearing bone are preferably dried and rigid, and will generally comprise between about 45% and 85% particulate mineral, for example, hydroxyapatite or tricalcium phosphate, or mixtures thereof. The tensile strength and rigidity may be further increased by heating the composition under vacuum at about 60°–90° C., preferably about 75° C., for about 5 to 15 hours, preferably about 10 hours.

Flexible sheets or membranous forms of glycosaminoglycan-synthetic polymer conjugates may be prepared by methods known in the art; for example, U.S. Pat. Nos. 4,600,533, 4,412,947, and 4,242,291. Briefly, an aqueous solution of glycosaminoglycan having a concentration in the range of approximately 10–100 mg/mL is east into the bottom of a flat container. A solution of activated polyethylene glycol is added to the glycosaminoglycan solution and allowed to react at room temperature for a period of time ranging from several hours to overnight. The resulting glycosaminoglycan-polymer conjugate is removed from the bottom of the container using a spatula and then washed with PBS to remove excess unreacted polymer.

The resulting conjugate composition may be compressed under constant pressure to form a uniform sheet or mat and optionally dehydrated under a vacuum oven or by lyophilization or air-drying to form a membrane of the invention. More flexible membranes can be obtained using lower glycosaminoglycan concentrations, higher synthetic polymer concentrations, and shorter reaction times.

Glycosaminoglycan-synthetic polymer conjugates may also be prepared in the form of sponges by lyophilizing an aqueous slurry of the composition after conjugation.

Glycosaminoglycan-synthetic polymer conjugate compositions can be formulated into hydrogels having moisture contents in the range of about 5 to about 95%. By varying the moisture content, hydrogels of varying density and stiffness may be obtained, depending on the desired end use application.

Glycosaminoglycan-synthetic polymer conjugates can be used to coat breast implants. The surface of a standard silicone shell implant can be chemically derivatized to provide active binding sites for di- or multifunctionally activated PEG-glycosaminoglycan (glycosaminoglycan-PEG-silicone). The presence of the conjugate coating bound directly to the silicone via activated PEG will reduce scar tissue formation and capsular contracture. Unlike typical coated implants, scar tissue will not be able to grow between the coating and the implant because the coating is conjugated directly to the surface of the implant.

Alternatively, a flexible sheet of glycosaminoglycan-synthetic polymer conjugate formulation can be formed into a hollow sphere for use as a breast implant shell. The shell can then be filled with a radiolucent material, such as a triglyceride, to facilitate mammography.

Formulations of glycosaminoglycan-synthetic polymer conjugates may also be used to coat other types of implants for long-term use in the body, such as catheters, cannulas, bone prostheses, cartilage replacements, minipumps and other drug delivery devices, artificial organs and blood vessels, meshes for tissue reinforcement, etc. Glycosaminoglycan-synthetic polymer compositions can also be used to coat platinum wires, which can then be administered to the site of an aneurysm via catheter. Such surface treatment renders the implants nonimmunogenic and reduces the incidence of foreign body reaction.

Coating of an implant with a conjugate composition may be accomplished by dipping the implant into a solution containing glycosaminoglycan and synthetic polymer while crosslinking is occurring and allowing the adherent viscous coating to dry as crosslinking is completed. One may pour, brush, or otherwise apply the reaction mixture to the implant if dipping is not feasible. Alternatively, one may use flexible sheets or membranous forms of the conjugate to wrap the object, sealing corners and edges with reaction mixture.

EXAMPLES

The following examples are set forth so as to provide those of ordinary skill in the art with a complete disclosure and description of how to make the conjugates and formulations and implants containing such conjugates and are not intended to limit the scope of the invention. Efforts have been made to ensure accuracy with respect to numbers used (e.g., amounts, temperature, molecular weight, etc.), but some experimental errors and deviation should be accounted for. Unless indicated otherwise, parts are parts by weight, molecular weight is average molecular weight, temperature is in degrees Centigrade, and pressure is at or near atmospheric.

Example 1

One (1) gram of sodium hyaluronate (obtained from LifeCore Biomedical) was added to 15 ml of 0.2M NaOH and allowed to dissolve overnight to form a homogeneous solution. Five (5) ml of the hyaluronic acid that was neutralized with 1M HCl solution was mixed with 50 mg of difunctionally activated S-PEG in 0.5 ml of PBS using syringe-to-syringe mixing.

The resulting material was extruded from the syringe into a petri dish and incubated at 37° C. After 16 hours, the material had formed a crosslinked gel.

Hyaluronic acid without S-PEG was used as a control in this experiment. After 16-hour incubation, the control was still liquid and runny.

Example 2

Forty (40) mg of difunctionally activated S-PEG was mixed with 145 ul of 1M HCl. After thorough mixing, the acidified S-PEG solution was drawn into a syringe.

A 6.6% (w/v) solution of deacetylated hyaluronic acid was prepared by mixing hyaluronic acid with 0.2M NaOH. The deacetylated hyaluronic acid solution (pH 13) was also transferred to a syringe.

The two syringes were then connected with a 3-way stopcock and the contents mixed using syringe-to-syringe mixing. Mixing the acidified S-PEG with the deacetylated hyaluronic acid caused the pH of the solution to neutralize and the crosslinking reaction to occur.

After mixing for 60–70 passes, the material was transferred to one syringe. The stopcock and the second (empty) syringe were removed. The material was now ready for injection and in situ crosslinking.

Example 3

One (1) milliliter of 35 mg/ml collagen in solution (pH 2) is mixed with 1 ml of a 2% (w/v) acidified solution of difunctionally activated S-PEG. The S-PEG- collagen solution is immediately mixed with 2 ml of a 10 mg/ml solution of deacetylated hyaluronic acid (pH 13), neutralizing the pH of the mixture and causing the difunctionally activated S-PEG to covalently bond with both the collagen and the hyaluronic acid.

Example 4

One (1) milliliter of 35 mg/ml Zyderm® I Collagen and 1 ml of a 10 mg/ml solution of hyaluronic acid are mixed together at pH 10. The collagen-hyaluronic acid solution is then mixed with 2 ml of a 2% (w/v) solution of difunctionally activated S-PEG in 0.1M HCl (pH 1), causing the solution to neutralize and crosslinking to occur between PEG, collagen, and hyaluronic acid.

Example 5

One (1) milliliter of 35 mg/ml Zyderm® I Collagen (pH 7) is mixed with 1 ml of a 10 mg/ml solution of deacetylated hyaluronic acid in 0.2M NaOH (pH 13). Two (2) milliliters of a 4% (w/v) solution of acidified difunctionally activated S-PEG is immediately added to neutralize the pH and effect crosslinking between the three components.

Example 6

One (1) milliliter of Zyderm® I Collagen and 1 ml of a 10 mg/mo solution of deacetylated hyaluronic acid are each adjusted to pH 9, then mixed together. The collagen-hyaluronic acid solution is then adjusted to approximately pH 7 by adding 0.1M HCl, causing the hyaluronic acid and collagen to form a weak gel due to ionic interaction. Subsequent addition of difunctionally activated S-PEG results in covalent crosslinking, producing a strong gel.

Example 7

(Coating of Implants)

Prepare a hyaluronic acid—S-PEG reaction mixture as described in Example 1. Dip a titanium implant into the reaction mixture immediately after crosslinking is initiated. Allow the implant coating to finish crosslinking, and dry overnight.

The present invention is shown and described herein at what is considered to be the most practical and preferred embodiments. It is recognized, however, that departures may be made therefrom which are within the scope of the invention and that obvious modifications will occur to one skilled in the art upon reading this disclosure.

What is claimed:

1. A biocompatible, biologically inert conjugate comprising a difunctionally activated hydrophilic synthetic polymer chemically conjugated to both collagen, or a derivative thereof, and to a glycosaminoglycan, or a derivative thereof.

2. The conjugate of claim 1, wherein the conjugate has the following structural formula:

GAG-HN-OC-(CH$_2$)$_n$-Z-PEG-Z-(CH$_2$)$_n$-CO-NH-COL wherein n is an integer ranging from 0 to about 4 and GAG is a glycosaminoglycan or a derivative thereof; COL is collagen, or a derivative thereof; and Z is O or O—C=O.

3. The conjugate of claim 2, wherein the glycosaminoglycan is selected from the group consisting of hyaluronic acid, the chondroitin sulfates, heparin, keratan sulfate, keratosulfate, chitin, chitosan 1, chitosan 2, and derivatives thereof, and mixtures of these glycosaminoglycans or their derivatives.

4. The conjugate of claim 2, wherein the collagen is selected from the group consisting of fibrillar collagen or nonfibrillar collagen.

5. The conjugate of claim 2, in a form selected from the group consisting of a membrane, bead, sponge, tube, sheet, and formed implant.

6. The conjugate of claim 2, in the form of a hydrogel composition having a moisture content in the range of from about 5% to about 95%.

7. The conjugate of claim 5, in the form of a formed implant for use in the repair, augmentation, or replacement of a body part selected from the group consisting of a heart valve, patella, ear, nose, and cheekbone.

8. The conjugate of claim 2, in the form of a bodily fluid replacement for joint fluid or vitreous humor.

\* \* \* \* \*